(12) United States Patent
Yang et al.

(10) Patent No.: US 10,736,996 B2
(45) Date of Patent: Aug. 11, 2020

(54) METHOD FOR CONSTRUCTING NITRIC OXIDE-GENERATING ADHERENT COATING

(71) Applicants: Chengdu Southwest Jiaotong University Science And Technology Garden Management Co., Ltd., Sichuan (CN); Chengdu Jiaoda Medical Science And Technology Company Limited, Chengdu, Sichuan (CN)

(72) Inventors: Zhilu Yang, Sichuan (CN); Nan Huang, Sichuan (CN); Jin Wang, Sichuan (CN); Yajun Weng, Sichuan (CN)

(73) Assignees: Chengdu Southwest Jiaotong University Science and, Sichuan (CN); Chengdu Jiaoda Medical Science And Technology Comp, Chengdu, Sichuan (CN)

( * ) Notice: Subject to any disclaimer, the term of this patent is extended or adjusted under 35 U.S.C. 154(b) by 21 days.

(21) Appl. No.: 15/503,172

(22) PCT Filed: Aug. 12, 2015

(86) PCT No.: PCT/CN2015/086773
§ 371 (c)(1),
(2) Date: Feb. 10, 2017

(87) PCT Pub. No.: WO2016/023494
PCT Pub. Date: Feb. 18, 2016

(65) Prior Publication Data
US 2017/0246353 A1 Aug. 31, 2017

(30) Foreign Application Priority Data
Aug. 12, 2014 (CN) .......................... 2014 1 0393735

(51) Int. Cl.
| | | |
|---|---|---|
| *A61L 31/10* | (2006.01) |
| *A61L 31/16* | (2006.01) |
| *A61K 33/00* | (2006.01) |
| *A61F 2/06* | (2013.01) |
| *C09D 7/40* | (2018.01) |
| *C09D 7/61* | (2018.01) |
| *A61L 27/34* | (2006.01) |
| *A61L 27/50* | (2006.01) |
| *A61L 27/54* | (2006.01) |
| *A61L 29/08* | (2006.01) |
| *A61L 29/16* | (2006.01) |
| *C09D 5/00* | (2006.01) |
| *C09D 177/04* | (2006.01) |
| *C09D 177/12* | (2006.01) |
| *C08K 5/13* | (2006.01) |
| *C08K 3/011* | (2018.01) |
| *A61M 25/00* | (2006.01) |
| *A61M 25/09* | (2006.01) |
| *C08K 3/16* | (2006.01) |

(52) U.S. Cl.
CPC ................ *A61L 31/10* (2013.01); *A61F 2/06* (2013.01); *A61K 33/00* (2013.01); *A61L 27/34* (2013.01); *A61L 27/507* (2013.01); *A61L 27/54* (2013.01); *A61L 29/085* (2013.01); *A61L 29/16* (2013.01); *A61L 31/16* (2013.01); *C09D 5/00* (2013.01); *C09D 7/40* (2018.01); *C09D 7/61* (2018.01); *C09D 177/04* (2013.01); *C09D 177/12* (2013.01); *A61L 2300/114* (2013.01); *A61L 2300/606* (2013.01); *A61L 2420/02* (2013.01); *A61M 2025/0046* (2013.01); *A61M 2025/09133* (2013.01); *C08K 3/011* (2018.01); *C08K 3/16* (2013.01); *C08K 5/13* (2013.01)

(58) Field of Classification Search
CPC ...................................................... A61L 31/10
See application file for complete search history.

(56) References Cited

U.S. PATENT DOCUMENTS

| | | | |
|---|---|---|---|
| 2007/0196424 A1 | 8/2007 | Glauser et al. | |
| 2008/0241208 A1* | 10/2008 | Shanley ................ | A61K 31/04 424/423 |

FOREIGN PATENT DOCUMENTS

| | | |
|---|---|---|
| CN | 101378792 A | 3/2009 |
| CN | 101420989 A | 4/2009 |
| CN | 101636187 A | 1/2010 |
| CN | 102961783 A | 3/2013 |
| CN | 104225675 A | 12/2014 |
| WO | WO 2007005910 A2 | 1/2017 |

OTHER PUBLICATIONS

International Search Report in corresponding PCT Application No. PCT/CN2015/086773, dated Nov. 17, 2015.

* cited by examiner

*Primary Examiner* — Dah-Wei D. Yuan
*Assistant Examiner* — Andrew J Bowman
(74) *Attorney, Agent, or Firm* — Leason Ellis LLP

(57) ABSTRACT

Disclosed is a method for preparing a nitric oxide-generating adherent coating, comprising: preparing a buffer solution containing polyphenol compounds, organic selenium or sulfur compounds and soluble copper salts; then contacting a base material with the solution, and washing and drying to obtain a target product. The nitric oxide-generating material prepared by the method can be used for any medical device, such as an intravascular stent, or materials and any complex-shaped base material, and has the capability of scavenging free radicals and catalyzing RSNO to produce nitrogen monoxide, and also has a response function of reduced glutathione (GSH), an antimicrobial function and all the physiological functions possessed by nitrogen monoxide.

5 Claims, No Drawings

METHOD FOR CONSTRUCTING NITRIC OXIDE-GENERATING ADHERENT COATING

CROSS-REFERENCE TO RELATED PATENT APPLICATIONS

This application is a U.S. National Phase Application under 35 U.S.C. § 371 of International Patent Application No. PCT/CN2015/086773, filed Aug. 12, 2015, and claims the priority of Chinese Application No. CN 201410393735.5, filed on Aug. 12, 2014, all of which are incorporated by reference in their entireties. The International Application was published on Feb. 18, 2016 as International Publication No. WO/2016/023494 A1.

TECHNICAL FIELD

The embodiments of the present invention relate to a technique for constructing a nitric oxide-generating adherent coating.

BACKGROUND

Cell signaling factor nitric oxide (NO) is mainly produced by action of arginine with nitrogen monoxide synthase secreted by endothelial cells (ECs). ECs are the main source of NO in the vascular system. The sustained release of NO is an important factor in maintaining cardiovascular homeostasis and regulating vasodilatation. In addition, NO has been proven to play an important role in preventing thrombosis, inhibiting proliferation and adhesion of smooth muscle cells (SMCs), and inhibiting leukocyte activation. NO also plays an important biological role in the immune response, anti-cancer, anti-bacterial and atherosclerosis treatment. NO also plays an important role in the mobilization, differentiation and function of endothelial progenitor cells (EPCs). Therefore, NO is a potentially ideal molecule for treating cardiovascular diseases, improving the biocompatibility of cardiovascular devices (such as vascular stents, artificial blood vessels, central venous catheters, oxygenators, etc.), designing antimicrobial materials and designing anticancer materials.

In the past 20 years, the research of NO-based clinical treatment mainly focused on developing effective NO-releasing and NO-generating materials. The challenge for NO-releasing materials primarily comprises short half-life of donor for NO production and uncertain safety dose for in vivo NO application, which is a major factor limiting its commercial use. However, long-term NO release is required for the coating of biomedical devices for long-term implantation such as vascular stents and artificial blood vessels, and depletion NO delivery systems are thus not ideal candidates. There is an endogenous NO donor nitrosothiol (RSNO) in the blood, for example, S-nitrosoglutathione (GSNO), S-nitrosocysteine (CysNO), and S-nitrosoalbumin (AlbSNO). Glutathione peroxidase (GPx) has been found to catalyze the decomposition of RSNO in the presence of thiol in vivo. Organic selenium compounds such as selenocystamine (SeCA) and 3,3'-diselenodipropionic acid (SeDPA), and organic sulfur compounds such as cystamine and cysteine have GPx-like activity to catalyze RSNO decomposition for NO production. Fixing an organic selenium compound or an organic sulfur compound onto the surface of a material is a conventional method for preparing a NO-generating material. However, there are many shortcomings of currently reported NO catalytically active materials. For example, the substance with the GPx-like catalytic activity is usually grafted onto a surface of a material, and the grafting amount depends on the number of functional groups on the surface of the material. However, the surface of most materials lacks functional groups, which leads to insufficient grafting of the GPx-like catalytically active molecules and insufficient catalyzed release of NO. In addition, most of the NO catalytically active materials do not have a strong binding site with the base material to be modified, resulting in poor stability and a shorter NO release cycle.

SUMMARY

One aspect of the present invention relates to a method of constructing a nitric oxide-generating adherent coating. The coating was prepared as follows:

A. The nitric oxide-generating adherent coating is obtained by a simple dip coating method. One or more polyphenol compound(s), one or more organic selenium or sulfur compound(s) that can catalyze nitrosothiol (RSNOs) to generate nitrogen monoxide, and one or more soluble copper salt(s) are dissolved in a buffer, and then the target object is brought into contact with the above mixed reaction solution.

B. After the reaction, the sample obtained from the step A is successively washed and dried to obtain a target modified material.

Another aspect of the present invention relates to a nitric oxide-generating adherent coating prepared by the above-described method.

Still another aspect of the invention relates to an article comprising a nitric oxide-generating adherent coating prepared by the above-described method.

DETAILED DESCRIPTION

In view of the shortcomings of the prior art, we have selected adhesion molecules such as polyphenol compounds, and substances with GPx-like catalytical activity such as organic selenium or sulfur compounds and copper ions or cuprous ions (derived from soluble copper salts) to prepare a NO-generating adherent coating which has a strong adhesion to the base material and has a long-term, stable, and controllable NO release rate. An embodiment of the present invention is achieved by the following means.

Disclosed is a method for constructing a nitric oxide-generating adherent coating. The coating is prepared from polyphenol(s), organic selenium or sulfur compound(s) and soluble copper salt(s). Formation of the nitric oxide-generating adherent coating is based on chemical coupling, coordination reaction and molecular self-assembly polymerization of polyphenol(s), organic selenium or sulfur compound(s) and soluble copper salt(s). The preparation process of the coating is as follows:

A. The nitric oxide-generating adherent coating is obtained by a simple dip coating method. One or more polyphenol(s), one or more organic selenium or sulfur compound(s) with a GPx-like activity, i.e., which can catalyze nitrosothiol (RSNOs) to generate nitrogen monoxide, and one or more soluble copper salt(s) are dissolved in a buffer, and then the target object is brought into contact with the above mixed reaction solution.

B. After the reaction, the samples obtained from the step A are successively washed and dried to obtain a target modified material.

In an embodiment of the present invention, contacting the target object with the mixed reaction solution can be achieved, for example, by immersion, coating or the like.

Polyphenol compound referred to in the embodiments of the present invention includes, but is not limited to, catechols, polyphenols, flavones, flavonols and flavanones.

The soluble copper salt referred to in the embodiments of the present invention includes, but is not limited to, soluble cuprous (I) salts and soluble copper (II) salts.

Catechols contemplated in the embodiments of the present invention include, but are not limited to, catechol, dopamine, norepinephrine, dopa, and caffeic acid. Polyphenols include, but are not limited to, epicatechin (EC), pyrogallol (PG), gallic acid (GA), gallocatechin gallate (EGCG), epicatechin gallate (ECG), epigallocatechin (EGC), derivatives of gallic acid, and tannic acid (TA). Flavones include, but are not limited to, chrysin, tectochrysin, acacetin, and apigenin. Flavonols include, but are not limited to, izalpinin, galangin, rhamnetin, isorhamnetin, rhamnocitrin, kaempferide, quercetin, delphinidin, theaflavin, baicalein, 5-pyrogalloic acid-2-ethylamine and myricetin. Flavanones include, but are not limited to, pinocembrin, sakuranetin, isosakuranetin and 4,5,7-trihydroxyflavanone.

Organic selenium compound referred to in the embodiments of the present invention includes, but is not limited to ebselen, SeCA (SeCA hydrochloride), selenocystine, selenocystamino acetic acid and selenomethionine. Organic sulfur compound includes, but is not limited to, cystamine (cystamine hydrochloride), cysteine, S-methyl-L-cysteine, S-ethyl-L-cysteine, S-allyl cysteine, S-allyl mercaptocysteine and γ-glutamine cysteamine.

The soluble copper salt referred to in the embodiments of the present invention includes, but is not limited to copper chloride ($CuCl_2$), cuprous chloride (CuCl), cuprous bromide (CuBr), copper bromide ($CuBr_2$), cuprous iodide (CuI), copper iodide ($CuI_2$), copper sulfate ($CuSO_4$), cuprous sulfate ($Cu_2SO_4$), copper nitrate ($Cu(NO_3)_2$), copper carbonate ($CuCO_3$), copper citrate ($C_6H_6CuO_7$), copper tartrate ($C_4H_4CuO_6.3H_2O$), copper propionate ($Cu(CO_2CH_3CH_2)_2$) and copper acetate ($Cu(CO_2CH_3)_2$).

The nitric oxide-generating adherent coating referred to in the embodiments of the present invention is applicable to almost all materials and any complex-shaped base material. Such materials involved in the embodiments of the present invention include, but are not limited to, stainless steel, cobalt based alloys, titanium and alloys thereof, nickel titanium alloys, tantalum and alloys thereof, magnesium and alloys thereof, iron and alloys thereof, zinc and alloys thereof, titanium oxide, carbonaceous material, silicon, silicon dioxide, hydroxyapatite, calcium phosphate, silicon nitride ($Si_3N_4$), silicon carbide (SiC), titanium nitride, terylene (PET), polyethylene (PE), polyvinyl chloride (PVC), polytetrafluoroethylene (PTFE), polyurethane (PU), polystyrene (PS), polyvinyl alcohol (PVALC), polypropylene (PP), polyoxymethylene (POM), polycarbonate (PC), polyglycolic acid (PGA), polymethylmethacrylate (PMMA), polyvinyl acetate (PVA), polylactic acid (PLA), poly(lactic-co-glycolic acid) (PLGA), polytrimethylene carbonate (PTMC), polycaprolactone (PCL), polyhydroxylkanoate (PHA), polybutylene succinate (PBS), animal derived acellular tissues and organs such as blood vessel, valve, heart, bone, lung, ligament, bladder, mucosa, and cornea. The NO-generating material disclosed by the embodiments of the present invention not only has the function of stable, long-term and controllable NO release, but also can be applied to surface modification of any medical device or material and any complex-shaped base material, such as vascular stents, intervention catheters and guidewires, artificial blood vessels, artificial hearts, artificial heart valves, catheters in contact with blood, hollow fiber membranes, oxygenators, dialyzers, $Fe_3O_4$ magnetic nanoparticles, mesoporous nanomaterials, central venous catheters, animal derived acellular tissues and organs such as blood vessel, valve, heart, bone, lung, ligament, bladder, mucosa, cornea and other materials or devices in contact with blood. The NO-generating material can be used for improving blood compatibility, selectively regulating growth behavior of endothelial cells, smooth muscle cells and inflammatory cells, scavenging free radicals and preventing atherosclerosis and other NO-related physiological functions. It is noteworthy that this type of NO-generating material can be firmly attached to the target object. In addition, because of its excellent antibacterial and osteoinductive formation effect, it is also suitable for surface modification of dental implant materials and osteoinductive materials.

The embodiments of the present invention are based on electrostatic self-assembly, covalent reaction (Michael addition and Schiff-base reaction) and coordination reaction which can effectively chelate organic selenium/sulfur compound containing amine/mercapto group and copper ions, forming a stable composite polymeric coating on the material or device surface.

The reaction of the embodiments of the present invention is carried out in a mild buffer. The buffer used may be, for example, a PBS buffer at pH 5-12 or a Bicine buffer at pH 5-12 or a Tris buffer at pH 5-12. The concentration of the polyphenol compound in the buffer may be from 0.1 ng/mL to 100 mg/mL. The concentration of the organic selenium or sulfur compound in the buffer may be from 0.1 ng/mL to 100 mg/mL. The concentration of the soluble copper salt in the buffer may be less than 100 mg/mL.

The reaction duration may be from less than 1 hour to several days. The reaction is usually carried out at room temperature, but it can also be carried out at an elevated temperature or at a reduced temperature.

Compared with the prior art, the embodiments of the invention have the advantages that:

1. Due to the strong adhesion of phenolic hydroxyl groups of the polyphenol compound among the reactants, the prepared NO-generating coating can be firmly bonded to surface of any medical device or material and any complex-shaped base material.

2. The NO release rate of the NO-generating coating disclosed in the embodiments of the present invention can be precisely controlled by adjusting the feed ratio of the reactants, i.e., the polyphenol compound(s), the organic selenium or sulfur compound(s) and the soluble copper salt(s).

3. Due to the presence of phenolic hydroxyl groups, S—S, Se—Se, copper ions/cuprous ions and contact with blood to catalytically produce NO, the NO-generating coating disclosed in the embodiments of the present invention has excellent free radical scavenging ability, reduced glutathione (GSH) response and antimicrobial function.

4. The method of preparing NO-generating coating disclosed in the embodiments of the present invention is simple and involves only one-step dip coating, i.e., bringing a target into contact with a mixed reaction solution of polyphenol compound(s), organic selenium or sulfur compound(s) and soluble copper salt(s). In addition, the reactants used to prepare the NO-generating coating are abundant in source and inexpensive.

5. The NO-generating coating disclosed in the embodiments of the present invention has multiple functions such as the ability to scavenge free radicals and catalyze the production of nitrogen monoxide by RSNO, the GSH response function and antimicrobial, immune and anti-cancer functions, as well as all the related physiological functions of NO. As such, its application prospect can be extended in different fields.

EXAMPLES

The examples described below are some embodiments of the present invention, but not all the embodiments of the present invention. Based on the described examples of the present invention, those skilled in the art, without inventive labor, can conceive of other embodiments, which are also within the scope of the present invention.

Example 1

A process for constructing a nitric oxide-generating adherent coating was as follows:

A. The nitric oxide-generating adherent coating could be applied to a 316L SS, CoCr alloy, tantalum alloy, magnesium alloy, iron or polymer vascular stent by simple dip coating. Dopa, SeCA and copper chloride were dissolved in a TRIS buffer of pH=5-12 to give a mixed solution in which each had a concentration of 1 mg/mL. The 316L SS, CoCr alloy, tantalum alloy, magnesium alloy, iron or polymer vascular stent was then immersed in the above mixed reaction solution and allowed to react at room temperature for 1 to 48 hours.

B. The 316L SS, CoCr alloy, tantalum alloy, magnesium alloy, iron or polymer vascular stent prepared by step A was washed and dried, thereby obtaining a 316L SS, CoCr alloy, tantalum alloy, magnesium alloy, iron or polymer vascular stent coated with a nitric oxide-generating coating.

Example 2

A process for constructing a nitric oxide-generating adherent coating was as follows:

A. The nitric oxide-generating adherent coating could be applied to a 316L SS, CoCr alloy, tantalum alloy, magnesium alloy, iron or polymer vascular stent by simple dip coating. Dopamine, SeCA and copper chloride were dissolved in a TRIS buffer of pH=5-12 to obtain a mixed solution in which each had a concentration of 1 mg/mL. The 316L SS, CoCr alloy, tantalum alloy, magnesium alloy, iron or polymer vascular stent was then immersed in the above mixed reaction solution and allowed to react at room temperature for 1 to 48 hours.

B. The 316L SS, CoCr alloy, tantalum alloy, magnesium alloy, iron or polymer vascular stent prepared by step A was washed and dried, thereby obtaining a 316L SS, CoCr alloy, tantalum alloy, magnesium alloy, iron or polymer vascular stent coated with a nitric oxide-generating coating.

Example 3

A process for constructing a nitric oxide-generating adherent coating was as follows:

A. The nitric oxide-generating adherent coating could be applied to a 316L SS, CoCr alloy, tantalum alloy, magnesium alloy, iron or polymer vascular stent by simple dip coating. Norepinephrine, SeCA and copper chloride were dissolved in a TRIS buffer of pH=5-12 to obtain a mixed solution in which each had a concentration of 1 mg/mL. The 316L SS, CoCr alloy, tantalum alloy, magnesium alloy, iron or polymer vascular stent was then immersed in the above mixed reaction solution and allowed to react at room temperature for 1 to 48 hours.

B. The 316L SS, CoCr alloy, tantalum alloy, magnesium alloy, iron or polymer vascular stent prepared by step A was washed and dried, thereby obtaining a 316L SS, CoCr alloy, magnesium alloy, iron or polymer vascular stent coated with a nitric oxide-generating coating.

Example 4

A process for constructing a nitric oxide-generating adherent coating was as follows:

A. The nitric oxide-generating adherent coating could be applied to a 316L SS, CoCr alloy, tantalum alloy, magnesium alloy, iron or polymer vascular stent by simple dip coating. EGCG, SeCA and copper chloride were dissolved in a TRIS buffer of pH=5-12 to obtain a mixed solution in which each had a concentration of 1 mg/mL. The 316L SS, CoCr alloy, tantalum alloy, magnesium alloy, iron or polymer vascular stent was then immersed in the above mixed reaction solution and allowed to react at room temperature for 1 to 48 hours.

B. The 316L SS, CoCr alloy, tantalum alloy, magnesium alloy, iron or polymer vascular stent prepared by step A was washed and dried, thereby obtaining a 316L SS, CoCr alloy, tantalum alloy, magnesium alloy, iron or polymer vascular stent coated with a nitric oxide-generating coating.

Example 5

A process for constructing a nitric oxide-generating adherent coating was as follows:

A. The nitric oxide-generating adherent coating could be applied to a 316L SS, CoCr alloy, tantalum alloy, magnesium alloy, zinc alloy, iron or polymer vascular stent by simple dip coating. Catechol, SeCA and copper chloride were dissolved in a TRIS buffer of pH=5-12 to obtain a mixed solution in which each had a concentration of 1 mg/mL. The 316L SS, CoCr alloy, tantalum alloy, magnesium alloy, zinc alloy, iron or polymer vascular stent was then immersed in the above mixed reaction solution and allowed to react at room temperature for 1 to 48 hours.

B. The 316L SS, CoCr alloy, tantalum alloy, magnesium alloy, zinc alloy, iron or polymer vascular stent prepared by step A was washed and dried, thereby obtaining a 316L SS, CoCr alloy, tantalum alloy, magnesium alloy, zinc alloy, iron or polymer vascular stent coated with a nitric oxide-generating coating.

Example 6

A process for constructing a nitric oxide-generating adherent coating was as follows:

A. The nitric oxide-generating adherent coating could be applied to a 316L SS, CoCr alloy, tantalum alloy, magnesium alloy, zinc alloy, iron or polymer vascular stent by simple dip coating. PG, SeCA and copper chloride were dissolved in a TRIS buffer of pH=5-12 to give a mixed solution in which each had a concentration of 1 mg/mL. The 316L SS, CoCr alloy, tantalum alloy, magnesium alloy, zinc alloy, iron or polymer vascular stent was then immersed in the above mixed reaction solution and allowed to react at room temperature for 1 to 48 hours.

B. The 316L SS, CoCr alloy, tantalum alloy, magnesium alloy, zinc alloy, iron or polymer vascular stent prepared by step A was washed and dried, thereby obtaining a 316L SS, CoCr alloy, tantalum alloy, magnesium alloy, zinc alloy, iron or polymer vascular stent coated with a nitric oxide-generating coating.

Example 7

A process for constructing a nitric oxide-generating adherent coating was as follows:

A. The nitric oxide-generating adherent coating could be applied to a 316L SS, CoCr alloy, magnesium alloy, iron or polymer vascular stent by simple dip coating. EC, SeCA and copper chloride were dissolved in a TRIS buffer of pH=5-12 to obtain a mixed solution in which each had a concentration of 1 mg/mL. The 316L SS, CoCr alloy, magnesium alloy, iron or polymer vascular stent was then immersed in the above mixed reaction solution and allowed to react at room temperature for 1 to 48 hours.

B. The 316L SS, CoCr alloy, magnesium alloy, iron or polymer vascular stent prepared by step A was washed and dried, thereby obtaining a 316L SS, CoCr alloy, magnesium alloy, iron or polymer vascular stent coated with a nitric oxide-generating coating.

Example 8

A process for constructing a nitric oxide-generating adherent coating was as follows:

A. The nitric oxide-generating adherent coating could be applied to a 316L SS, CoCr alloy, magnesium alloy, iron or polymer vascular stent by simple dip coating. ECG, SeCA and copper chloride were dissolved in a TRIS buffer of pH=5-12 to obtain a mixed solution in which each had a concentration of 1 mg/mL. The 316L SS, CoCr alloy, magnesium alloy, iron or polymer vascular stent was then immersed in the above mixed reaction solution and allowed to react at room temperature for 1 to 48 hours.

B. The 316L SS, CoCr alloy, magnesium alloy, iron or polymer vascular stent prepared by step A was washed and dried, thereby obtaining a 316L SS, CoCr alloy, magnesium alloy, iron or polymer vascular stent coated with a nitric oxide-generating coating.

Example 9

A process for constructing a nitric oxide-generating adherent coating was as follows:

A. The nitric oxide-generating adherent coating could be applied to a 316L SS, CoCr alloy, magnesium alloy, iron or polymer vascular stent by simple dip coating. EGC, SeCA and copper chloride were dissolved in a TRIS buffer of pH=5-12 to obtain a mixed solution in which each had a concentration of 1 mg/mL. The 316L SS, CoCr alloy, magnesium alloy, iron or polymer vascular stent was then immersed in the above mixed reaction solution and allowed to react at room temperature for 1 to 48 hours.

B. The 316L SS, CoCr alloy, magnesium alloy, iron or polymer vascular stent prepared by step A was washed and dried, thereby obtaining a 316L SS, CoCr alloy, magnesium alloy, iron or polymer vascular stent coated with a nitric oxide-generating coating.

Example 10

A process for constructing a nitric oxide-generating adherent coating was as follows:

A. The nitric oxide-generating adherent coating could be applied to an artificial blood vessel, an artificial heart, and an artificial heart valve by simple dip coating. Dopa, SeCA and copper chloride were dissolved in a TRIS buffer of pH=5-12 to give a mixed solution in which each had a concentration of 1 mg/mL. The artificial blood vessel, the artificial heart, or the artificial heart valve was then brought into contact with the above mixed reaction solution and allowed to react at room temperature for 1 to 48 hours.

B. The artificial blood vessel, the artificial heart or the artificial heart valve prepared in the step A was washed and dried, thereby obtaining an artificial blood vessel, an artificial heart, or an artificial heart valve coated with a nitric oxide-generating coating.

Example 11

A process for constructing a nitric oxide-generating adherent coating was as follows:

A. The nitric oxide-generating adherent coating could be applied to an artificial blood vessel, an artificial heart, or an artificial heart valve by simple dip coating. Dopamine, SeCA and copper chloride were dissolved in a TRIS buffer of pH=5-12 to obtain a mixed solution in which each had a concentration of 1 mg/mL. The artificial blood vessel, the artificial heart, or the artificial heart valve was then contacted with the above mixed reaction solution and allowed to react at room temperature for 1 to 48 hours.

B. The artificial blood vessel, the artificial heart or the artificial heart valve prepared in the step A was washed and dried, thereby obtaining an artificial blood vessel, an artificial heart, or an artificial heart valve coated with a nitric oxide-generating coating.

Example 12

A process for constructing a nitric oxide-generating adherent coating was as follows:

A. The nitric oxide-generating adherent coating could be applied to an artificial blood vessel, an artificial heart, and an artificial heart valve by simple dip coating. Norepinephrine, SeCA and copper chloride were dissolved in a TRIS buffer of pH=5-12 to obtain a mixed solution in which each had a concentration of 1 mg/mL. The artificial blood vessel, the artificial heart, or the artificial heart valve was then contacted with the above mixed reaction solution and allowed to react at room temperature for 1 to 48 hours.

B. The artificial blood vessel, the artificial heart or the artificial heart valve prepared in the step A was washed and dried, thereby obtaining an artificial blood vessel, an artificial heart, or an artificial heart valve coated with a nitric oxide-generating coating.

Example 13

A process for constructing a nitric oxide-generating adherent coating was as follows:

A. The nitric oxide-generating adherent coating could be applied to an artificial blood vessel, an artificial heart, and an artificial heart valve by simple dip coating. EGCG, SeCA and copper chloride were dissolved in a TRIS buffer of pH=5-12 to obtain a mixed solution in which each had a concentration of 1 mg/mL. The artificial blood vessel, the artificial heart, or the artificial heart valve was then contacted with the above mixed reaction solution and allowed to react at room temperature for 1 to 48 hours.

B. The artificial blood vessel, the artificial heart or the artificial heart valve prepared in the step A was washed and dried, thereby obtaining an artificial blood vessel, an artificial heart, or an artificial heart valve coated with a nitric oxide-generating coating.

Example 14

A process for constructing a nitric oxide-generating adherent coating was as follows:

A. The nitric oxide-generating adherent coating could be applied to an artificial blood vessel, an artificial heart, and an artificial heart valve by simple dip coating. Catechol, SeCA and copper chloride were dissolved in a TRIS buffer of pH=5-12 to obtain a mixed solution in which each had a concentration of 1 mg/mL. The artificial blood vessel, the artificial heart, or the artificial heart valve was then contacted with the above mixed reaction solution and allowed to react at room temperature for 1 to 48 hours.

B. The artificial blood vessel, the artificial heart, or the artificial heart valve prepared by step A was washed and dried, thereby obtaining an artificial blood vessel, an artificial heart and an artificial heart valve coated with a nitric oxide-generating coating.

Example 15

A process for constructing a nitric oxide-generating adherent coating was as follows:

A. The nitric oxide-generating adherent coating could be applied to an artificial blood vessel, an artificial heart, and an artificial heart valve by simple dip coating. PG, SeCA and copper chloride were dissolved in a TRIS buffer of pH=5-12 to give a mixed solution in which each had a concentration of 1 mg/mL. The artificial blood vessel, the artificial heart, or the artificial heart valve was then brought into contact with the above mixed reaction solution and allowed to react at room temperature for 1 to 48 hours.

B. The artificial blood vessel, the artificial heart or the artificial heart valve prepared in the step A was washed and dried, thereby obtaining an artificial blood vessel, an artificial heart, or an artificial heart valve coated with a nitric oxide-generating coating.

Example 16

A process for constructing a nitric oxide-generating adherent coating was as follows:

A. The nitric oxide-generating adherent coating could be applied to an artificial blood vessel, an artificial heart, and an artificial heart valve by simple dip coating. EC, SeCA and copper chloride were dissolved in a TRIS buffer of pH=5-12 to obtain a mixed solution in which each had a concentration of 1 mg/mL. The artificial blood vessel, the artificial heart, or the artificial heart valve was then contacted with the above mixed reaction solution and allowed to react at room temperature for 1 to 48 hours.

B. The artificial blood vessel, the artificial heart or the artificial heart valve prepared in the step A was washed and dried, thereby obtaining an artificial blood vessel, an artificial heart, or an artificial heart valve coated with a nitric oxide-generating coating.

Example 17

A process for constructing a nitric oxide-generating adherent coating was as follows:

A. The nitric oxide-generating adherent coating could be applied to an artificial blood vessel, an artificial heart, and an artificial heart valve by simple dip coating. ECG, SeCA and copper chloride were dissolved in a TRIS buffer of pH=5-12 to obtain a mixed solution in which each had a concentration of 1 mg/mL. The artificial blood vessel, the artificial heart, or the artificial heart valve was then contacted with the above mixed reaction solution and allowed to react at room temperature for 1 to 48 hours.

B. The artificial blood vessel, the artificial heart or the artificial heart valve prepared in the step A was washed and dried, thereby obtaining an artificial blood vessel, an artificial heart, or an artificial heart valve coated with a nitric oxide-generating coating.

Example 18

A process for constructing a nitric oxide-generating adherent coating was as follows:

A. The nitric oxide-generating adherent coating could be applied to an artificial blood vessel, an artificial heart, and an artificial heart valve by simple dip coating. EGC, SeCA and copper chloride were dissolved in a TRIS buffer of pH=5-12 to obtain a mixed solution in which each had a concentration of 1 mg/mL. The artificial blood vessel, the artificial heart, or the artificial heart valve was then contacted with the above mixed reaction solution and allowed to react at room temperature for 1 to 48 hours.

B. The artificial blood vessel, the artificial heart or the artificial heart valve prepared in the step A was washed and dried, thereby obtaining an artificial blood vessel, an artificial heart, or an artificial heart valve coated with a nitric oxide-generating coating.

Example 19

A process for constructing a nitric oxide-generating adherent coating was as follows:

A. The nitric oxide-generating adherent coating could be applied to an extracorporeal circulation catheter or a central venous catheter by simple dip coating. Dopa, SeCA and copper chloride were dissolved in a TRIS buffer of pH=5-12 to give a mixed solution in which each had a concentration of 1 mg/mL. The extracorporeal circulation catheter or central venous catheter was then immersed in the above mixed reaction solution and allowed to react at room temperature for 1 to 48 hours.

B. The extracorporeal circulation catheter or central venous catheter prepared by step A was washed and dried, thereby obtaining an extracorporeal circulation catheter or a central venous catheter coated with a nitric oxide-generating coating.

Example 20

A process for constructing a nitric oxide-generating adherent coating was as follows:

A. The nitric oxide-generating adherent coating could be applied to an extracorporeal circulation catheter or a central venous catheter by simple dip coating. Dopamine, SeCA and copper chloride were dissolved in a TRIS buffer of pH=5-12 to obtain a mixed solution in which each had a concentration of 1 mg/mL. The extracorporeal circulation catheter or central venous catheter was then immersed in the above mixed reaction solution and allowed to react at room temperature for 1 to 48 hours.

B. The extracorporeal circulation catheter or central venous catheter prepared by step A was washed and dried, thereby obtaining an extracorporeal circulation catheter or a central venous catheter coated with a nitric oxide-generating coating.

Example 21

A process for constructing a nitric oxide-generating adherent coating was as follows:

A. The nitric oxide-generating adherent coating could be applied to a medical catheter, an oxygenator, or a dialyzer by a simple dip coating method. Norepinephrine, SeCA and copper chloride were dissolved in a TRIS buffer of pH=5-12 to obtain a mixed solution in which each had a concentration of 1 mg/mL. Then, the medical catheter, the oxygenator, or the dialyzer was brought into contact with the above mixed reaction solution, and allowed to react at room temperature for 1 to 48 hours.

B. The medical catheter, oxygenator, or dialyzer prepared by step A was washed and dried, thereby obtaining a medical catheter, an oxygenator, or a dialyzer coated with a nitric oxide-generating coating.

Example 22

A process for constructing a nitric oxide-generating adherent coating was as follows:

A. The nitric oxide-generating adherent coating could be applied to a medical catheter, an oxygenator, or a dialyzer by a simple dip coating method. EGCG, SeCA and copper chloride were dissolved in a TRIS buffer of pH=5-12 to obtain a mixed solution in which each had a concentration of 1 mg/mL. The medical catheter, the oxygenator, or the dialyzer was then brought into contact with the above mixed reaction solution, and allowed to react at room temperature for 1 to 48 hours.

B. The medical catheter, oxygenator, or dialyzer prepared by step A was washed and dried, thereby obtaining a medical catheter, an oxygenator, or a dialyzer coated with a nitric oxide-generating coating.

Example 23

A process for constructing a nitric oxide-generating adherent coating was as follows:

A. The nitric oxide-generating adherent coating could be applied to a medical catheter, an oxygenator, or a dialyzer by a simple dip coating method. Catechol, SeCA and copper chloride were dissolved in a TRIS buffer of pH=5-12 to obtain a mixed solution in which each had a concentration of 1 mg/mL. Then, the medical catheter, the oxygenator, or the dialyzer was brought into contact with the above mixed reaction solution, and allowed to react at room temperature for 1 to 48 hours.

B. The medical catheter, oxygenator, or dialyzer prepared by step A was washed and dried, thereby obtaining a medical catheter, an oxygenator, or a dialyzer coated with a nitric oxide-generating coating.

Example 24

A process for constructing a nitric oxide-generating adherent coating was as follows:

A. The nitric oxide-generating adherent coating could be applied to a medical catheter, an oxygenator, or a dialyzer by a simple dip coating method. PG, SeCA and copper chloride were dissolved in a TRIS buffer of pH=5-12 to give a mixed solution in which each had a concentration of 1 mg/mL. Then, the medical catheter, the oxygenator, or the dialyzer was brought into contact with the above mixed reaction solution, and allowed to react at room temperature for 1 to 48 hours.

B. The medical catheter, oxygenator, or dialyzer prepared by step A was washed and dried, thereby obtaining a medical catheter, an oxygenator, or a dialyzer coated with a nitric oxide-generating coating.

Example 25

A process for constructing a nitric oxide-generating adherent coating was as follows:

A. The nitric oxide-generating adherent coating could be applied to a medical catheter, an oxygenator, or a dialyzer by a simple dip coating method. EC, SeCA and copper chloride were dissolved in a TRIS buffer of pH=5-12 to obtain a mixed solution in which each had a concentration of 1 mg/mL. Then, the medical catheter, the oxygenator, or the dialyzer was brought into contact with the above mixed reaction solution, and allowed to react at room temperature for 1 to 48 hours.

B. The medical catheter, oxygenator, or dialyzer prepared by step A was washed and dried, thereby obtaining a medical catheter, an oxygenator, or a dialyzer coated with a nitric oxide-generating coating.

Example 26

A process for constructing a nitric oxide-generating adherent coating was as follows:

A. The nitric oxide-generating adherent coating could be applied to a medical catheter, an oxygenator, or a dialyzer by a simple dip coating method. ECG, SeCA and copper chloride were dissolved in a TRIS buffer of pH=5-12 to obtain a mixed solution in which each had a concentration of 1 mg/mL. Then, the medical catheter, the oxygenator, or the dialyzer was brought into contact with the above mixed reaction solution, and allowed to react at room temperature for 1 to 48 hours.

B. The medical catheter, the oxygenator, or the dialyzer prepared by step A was washed and dried, thereby obtaining a medical catheter, an oxygenator, or a dialyzer coated with a nitric oxide-generating coating.

Example 27

A process for constructing a nitric oxide-generating adherent coating was as follows:

A. The nitric oxide-generating adherent coating could be applied to a medical catheter, an oxygenator, or a dialyzer by a simple dip coating method. EGC, SeCA and copper chloride were dissolved in a TRIS buffer of pH=5-12 to obtain a mixed solution in which each had a concentration of 1 mg/mL. Then, the medical catheter, the oxygenator, or the dialyzer was brought into contact with the above mixed reaction solution, and allowed to react at room temperature for 1 to 48 hours.

B. The medical catheter, oxygenator, or dialyzer prepared by step A was washed and dried, thereby obtaining a medical catheter, an oxygenator, or a dialyzer coated with a nitric oxide-generating coating.

Example 28

A process for constructing a nitric oxide-generating adherent coating was as follows:

A. The nitric oxide-generating adherent coating could be applied to a 316L SS, CoCr alloy, magnesium alloy, iron or polymer vascular stent by simple dip coating. Dopa, cystamine and copper sulfate were dissolved in a TRIS buffer of pH=5-12 to obtain a mixed solution in which each had a concentration of 1 mg/mL. The 316L SS, CoCr alloy, magnesium alloy, iron or polymer vascular stent was then immersed in the above mixed reaction solution and allowed to react at room temperature for 1 to 48 hours.

B. The 316L SS, CoCr alloy, magnesium alloy, iron or polymer vascular stent prepared by step A was washed and dried, thereby obtaining a 316L SS, CoCr alloy, magnesium alloy, iron or polymer vascular stent coated with a nitric oxide-generating coating.

Example 29

A process for constructing a nitric oxide-generating adherent coating was as follows:

A. The nitric oxide-generating adherent coating could be applied to a 316L SS, CoCr alloy, magnesium alloy, iron or polymer vascular stent by simple dip coating. Dopamine, cystamine and copper sulfate were dissolved in a TRIS buffer of pH=5-12 to give a mixed solution in which each had a concentration of 1 mg/mL. The 316L SS, CoCr alloy, magnesium alloy, iron or polymer vascular stent was then immersed in the above mixed reaction solution and allowed to react at room temperature for 1 to 48 hours.

B. The 316L SS, CoCr alloy, magnesium alloy, iron or polymer vascular stent prepared by step A was washed and dried, thereby obtaining a 316L SS, CoCr alloy, magnesium alloy, iron or polymer vascular stent coated with a nitric oxide-generating coating.

Example 30

A process for constructing a nitric oxide-generating adherent coating was as follows:

A. The nitric oxide-generating adherent coating could be applied to a 316L SS, CoCr alloy, magnesium alloy, iron or polymer vascular stent by simple dip coating. Norepinephrine, cystamine and copper sulfate were dissolved in a TRIS buffer of pH=5-12 to obtain a mixed solution in which each had a concentration of 1 mg/mL. The 316L SS, CoCr alloy, magnesium alloy, iron or polymer vascular stent was then immersed in the above mixed reaction solution and allowed to react at room temperature for 1 to 48 hours.

B. The 316L SS, CoCr alloy, magnesium alloy, iron or polymer vascular stent prepared by step A was washed and dried, thereby obtaining a 316L SS, CoCr alloy, magnesium alloy, iron or polymer vascular stent coated with a nitric oxide-generating coating.

Example 31

A process for constructing a nitric oxide-generating adherent coating was as follows:

A. The nitric oxide-generating adherent coating could be applied to a 316L SS, CoCr alloy, magnesium alloy, iron or polymer vascular stent by simple dip coating. EGCG, cystamine and copper sulfate were dissolved in a TRIS buffer of pH=5-12 to obtain a mixed solution in which each had a concentration of 1 mg/mL. The 316L SS, CoCr alloy, magnesium alloy, iron or polymer vascular stent was then immersed in the above mixed reaction solution and allowed to react at room temperature for 1 to 48 hours.

B. The 316L SS, CoCr alloy, magnesium alloy, iron or polymer vascular stent prepared by step A was washed and dried, thereby obtaining a 316L SS, CoCr alloy, magnesium alloy, iron or polymer vascular stent coated with a nitric oxide-generating coating.

Example 32

A process for constructing a nitric oxide-generating adherent coating was as follows:

A. The nitric oxide-generating adherent coating could be applied to a 316L SS, CoCr alloy, magnesium alloy, iron or polymer vascular stent by simple dip coating. Catechol, cystamine and copper sulfate were dissolved in a TRIS buffer of pH=5-12 to give a mixed solution in which each had a concentration of 1 mg/mL. The 316L SS, CoCr alloy, magnesium alloy, iron or polymer vascular stent was then immersed in the above mixed reaction solution and allowed to react at room temperature for 1 to 48 hours.

B. The 316L SS, CoCr alloy, magnesium alloy, iron or polymer vascular stent prepared by step A was washed and dried, thereby obtaining a 316L SS, CoCr alloy, magnesium alloy, iron or polymer vascular stent coated with a nitric oxide-generating coating.

Example 33

A process for constructing a nitric oxide-generating adherent coating was as follows:

A. The nitric oxide-generating adherent coating could be applied to a 316L SS, CoCr alloy, magnesium alloy, iron or polymer vascular stent by simple dip coating. PG, cystamine and copper sulfate were dissolved in a TRIS buffer of pH=5-12 to give a mixed solution in which each had a concentration of 1 mg/mL. The 316L SS, CoCr alloy, magnesium alloy, iron or polymer vascular stent was then immersed in the above mixed reaction solution and allowed to react at room temperature for 1 to 48 hours.

B. The 316L SS, CoCr alloy, magnesium alloy, iron or polymer vascular stent prepared by step A was washed and dried, thereby obtaining a 316L SS, CoCr alloy, magnesium alloy, iron or polymer vascular stent coated with a nitric oxide-generating coating.

Example 34

A process for constructing a nitric oxide-generating adherent coating was as follows:

A. The nitric oxide-generating adherent coating could be applied to a 316L SS, CoCr alloy, magnesium alloy, iron or polymer vascular stent by simple dip coating. EC, cystamine and copper sulfate were dissolved in the TRIS buffer of pH=5-12 to obtain a mixed solution in which each had a concentration of 1 mg/mL. The 316L SS, CoCr alloy, magnesium alloy, iron or polymer vascular stent was then immersed in the above mixed reaction solution and allowed to react at room temperature for 1 to 48 hours.

B. The 316L SS, CoCr alloy, magnesium alloy, iron or polymer vascular stent prepared by step A was washed and dried, thereby obtaining a 316L SS, CoCr alloy, magnesium alloy, iron or polymer vascular stent coated with a nitric oxide-generating coating.

Example 35

A process for constructing a nitric oxide-generating adherent coating was as follows:

A. The nitric oxide-generating adherent coating could be applied to a 316L SS, CoCr alloy, magnesium alloy, iron or polymer vascular stent by simple dip coating. ECG, cystamine and copper sulfate were dissolved in a TRIS buffer of pH=5-12 to obtain a mixed solution in which each had a concentration of 1 mg/mL. The 316L SS, CoCr alloy, magnesium alloy, iron or polymer vascular stent was then immersed in the above mixed reaction solution and allowed to react at room temperature for 1 to 48 hours.

B. The 316L SS, CoCr alloy, magnesium alloy, iron or polymer vascular stent prepared by step A was washed and dried, thereby obtaining a 316L SS, CoCr alloy, magnesium alloy, iron or polymer vascular stent coated with a nitric oxide-generating coating.

Example 36

A process for constructing a nitric oxide-generating adherent coating was as follows:

A. The nitric oxide-generating adherent coating could be applied to a 316L SS, CoCr alloy, magnesium alloy, iron or polymer vascular stent by simple dip coating. EGC, cystamine and copper sulfate were dissolved in a TRIS buffer of pH=5-12 to obtain a mixed solution in which each had a concentration of 1 mg/mL. The 316L SS, CoCr alloy, magnesium alloy, iron or polymer vascular stent was then immersed in the above mixed reaction solution and allowed to react at room temperature for 1 to 48 hours.

B. The 316L SS, CoCr alloy, magnesium alloy, iron or polymer vascular stent prepared by step A was washed and dried, thereby obtaining a 316L SS, CoCr alloy, magnesium alloy, iron or polymer vascular stent coated with a nitric oxide-generating coating.

Example 37

A process for constructing a nitric oxide-generating adherent coating was as follows:

A. The nitric oxide-generating adherent coating could be applied to an artificial blood vessel by a simple dip coating method. Dopa, cystamine and copper sulfate were dissolved in a TRIS buffer of pH=5-12 to obtain a mixed solution in which each had a concentration of 1 mg/mL. Then, the artificial blood vessel was immersed in the above-mentioned mixed reaction solution, and allowed to react at room temperature for 1 to 48 hours.

B. The artificial blood vessel prepared by step A was washed and dried, thereby obtaining an artificial blood vessel coated with a nitric oxide-generating coating.

Example 38

A process for constructing a nitric oxide-generating adherent coating was as follows:

A. The nitric oxide-generating adherent coating could be applied to an artificial blood vessel by a simple dip coating method. Dopamine, cystamine and copper sulfate were dissolved in a TRIS buffer of pH=5-12 to give a mixed solution in which each had a concentration of 1 mg/mL. Then, the artificial blood vessel was immersed in the above-mentioned mixed reaction solution, and allowed to react at room temperature for 1 to 48 hours.

B. The artificial blood vessel prepared by step A was washed and dried, thereby obtaining an artificial blood vessel coated with a nitric oxide-generating coating.

Example 39

A process for constructing a nitric oxide-generating adherent coating was as follows:

A. The nitric oxide-generating adherent coating could be applied to an artificial blood vessel by a simple dip coating method. Norepinephrine, cystamine and copper sulfate were dissolved in a TRIS buffer of pH=5-12 to obtain a mixed solution in which each had a concentration of 1 mg/mL. Then, the artificial blood vessel was immersed in the above-mentioned mixed reaction solution, and allowed to react at room temperature for 1 to 48 hours.

B. The artificial blood vessel prepared by step A was washed and dried, thereby obtaining an artificial blood vessel coated with a nitric oxide-generating coating.

Example 40

A process for constructing a nitric oxide-generating adherent coating was as follows:

A. The nitric oxide-generating adherent coating could be applied to an artificial blood vessel by a simple dip coating method. EGCG, cystamine and copper sulfate were dissolved in a TRIS buffer of pH=5-12 to obtain a mixed solution in which each had a concentration of 1 mg/mL. Then, the artificial blood vessel was immersed in the above-mentioned mixed reaction solution, and allowed to react at room temperature for 1 to 48 hours.

B. The artificial blood vessel prepared by step A was washed and dried, thereby obtaining an artificial blood vessel coated with a nitric oxide-generating coating.

Example 41

A process for constructing a nitric oxide-generating adherent coating was as follows:

A. The nitric oxide-generating adherent coating could be applied to an artificial blood vessel by a simple dip coating method. Catechol, cystamine and copper sulfate were dissolved in a TRIS buffer of pH=5-12 to give a mixed solution in which each had a concentration of 1 mg/mL. Then, the artificial blood vessel was immersed in the above-mentioned mixed reaction solution, and allowed to react at room temperature for 1 to 48 hours.

B. The artificial blood vessel prepared by step A was washed and dried, thereby obtaining an artificial blood vessel coated with a nitric oxide-generating coating.

Example 42

A process for constructing a nitric oxide-generating adherent coating was as follows:

A. The nitric oxide-generating adherent coating could be applied to an artificial blood vessel by a simple dip coating method. PG, cystamine and copper sulfate were dissolved in a TRIS buffer of pH=5-12 to give a mixed solution in which each had a concentration of 1 mg/mL. Then, the artificial blood vessel was immersed in the above-mentioned mixed reaction solution, and allowed to react at room temperature for 1 to 48 hours.

B. The artificial blood vessel prepared by step A was washed and dried, thereby obtaining an artificial blood vessel coated with a nitric oxide-generating coating.

Example 43

A process for constructing a nitric oxide-generating adherent coating was as follows:

A. The nitric oxide-generating adherent coating could be applied to an artificial blood vessel by a simple dip coating method. EC, cystamine and copper sulfate were dissolved in the TRIS buffer of pH=5-12 to obtain a mixed solution in which each had a concentration of 1 mg/mL. Then, the artificial blood vessel was immersed in the above-mentioned mixed reaction solution, and allowed to react at room temperature for 1 to 48 hours.

B. The artificial blood vessel prepared by step A was washed and dried, thereby obtaining an artificial blood vessel coated with a nitric oxide-generating coating.

Example 44

A process for constructing a nitric oxide-generating adherent coating was as follows:
A. The nitric oxide-generating adherent coating could be applied to an artificial blood vessel by a simple dip coating method. ECG, cystamine and copper sulfate were dissolved in a TRIS buffer of pH=5-12 to obtain a mixed solution in which each had a concentration of 1 mg/mL. Then, the artificial blood vessel was immersed in the above-mentioned mixed reaction solution, and allowed to react at room temperature for 1 to 48 hours.
B. The artificial blood vessel prepared by step A was washed and dried, thereby obtaining an artificial blood vessel coated with a nitric oxide-generating coating.

Example 45

A process for constructing a nitric oxide-generating adherent coating was as follows:
A. The nitric oxide-generating adherent coating could be applied to an artificial blood vessel by a simple dip coating method. EGC, cystamine and copper sulfate were dissolved in a TRIS buffer of pH=5-12 to obtain a mixed solution in which each had a concentration of 1 mg/mL. Then, the artificial blood vessel was immersed in the above-mentioned mixed reaction solution, and allowed to react at room temperature for 1 to 48 hours.
B. The artificial blood vessel prepared by step A was washed and dried, thereby obtaining an artificial blood vessel coated with a nitric oxide-generating coating.

Example 46

A process for constructing a nitric oxide-generating adherent coating was as follows:
A. The nitric oxide-generating adherent coating could be applied to a medical catheter, an oxygenator, or a dialyzer by a simple dip coating method. Dopa, cystamine and copper sulfate were dissolved in a TRIS buffer of pH=5-12 to obtain a mixed solution in which each had a concentration of 1 mg/mL. Then, the medical catheter, the oxygenator, or the dialyzer was brought into contact with the above mixed reaction solution, and allowed to react at room temperature for 1 to 48 hours.
B. The medical catheter, oxygenator, or dialyzer prepared by step A was washed and dried, thereby obtaining a medical catheter, an oxygenator, or a dialyzer coated with a nitric oxide-generating coating.

Example 47

A process for constructing a nitric oxide-generating adherent coating was as follows:
A. The nitric oxide-generating adherent coating could be applied to a medical catheter, an oxygenator, or a dialyzer by a simple dip coating method. Dopamine, cystamine and copper sulfate were dissolved in a TRIS buffer of pH=5-12 to give a mixed solution in which each had a concentration of 1 mg/mL. Then, the medical catheter, the oxygenator, or the dialyzer was brought into contact with the above mixed reaction solution, and allowed to react at room temperature for 1 to 48 hours.
B. The medical catheter, oxygenator, or dialyzer prepared by step A was washed and dried, thereby obtaining a medical catheter, an oxygenator, or a dialyzer coated with a nitric oxide-generating coating.

Example 48

A process for constructing a nitric oxide-generating adherent coating was as follows:
A. The nitric oxide-generating adherent coating could be applied to a medical catheter, an oxygenator, or a dialyzer by a simple dip coating method. Norepinephrine, cystamine and copper sulfate were dissolved in a TRIS buffer of pH=5-12 to obtain a mixed solution in which each had a concentration of 1 mg/mL. Then, the medical catheter, the oxygenator, or the dialyzer was brought into contact with the above mixed reaction solution, and allowed to react at room temperature for 1 to 48 hours.
B. The medical catheter, oxygenator, or dialyzer prepared by step A was washed and dried, thereby obtaining a medical catheter, an oxygenator, or a dialyzer coated with a nitric oxide-generating coating.

Example 49

A process for constructing a nitric oxide-generating adherent coating was as follows:
A. The nitric oxide-generating adherent coating could be applied to a medical catheter, an oxygenator, or a dialyzer by a simple dip coating method. EGCG, cystamine and copper sulfate were dissolved in a TRIS buffer of pH=5-12 to obtain a mixed solution in which each had a concentration of 1 mg/mL. The medical catheter, the oxygenator, or the dialyzer was then brought into contact with the above mixed reaction solution and allowed to react at room temperature for 1 to 48 hours.
B. The medical catheter, oxygenator, or dialyzer prepared by step A was washed and dried, thereby obtaining a medical catheter, an oxygenator, or a dialyzer coated with a nitric oxide-generating coating.

Example 50

A process for constructing a nitric oxide-generating adherent coating was as follows:
A. The nitric oxide-generating adherent coating could be applied to a medical catheter, an oxygenator, or a dialyzer by a simple dip coating method. Catechol, cystamine and copper sulfate were dissolved in a TRIS buffer of pH=5-12 to give a mixed solution in which each had a concentration of 1 mg/mL. Then, the medical catheter, the oxygenator, or the dialyzer was brought into contact with the above mixed reaction solution, and allowed to react at room temperature for 1 to 48 hours.
B. The medical catheter, oxygenator, or dialyzer prepared by step A was washed and dried, thereby obtaining a medical catheter, an oxygenator, or a dialyzer coated with a nitric oxide-generating coating.

Example 51

A process for constructing a nitric oxide-generating adherent coating was as follows:
A. The nitric oxide-generating adherent coating could be applied to a medical catheter, an oxygenator, or a dialyzer by a simple dip coating method. PG, cystamine and copper sulfate were dissolved in a TRIS buffer of pH=5-12 to give a mixed solution in which each had a concentration of 1 mg/mL. Then, the medical catheter, the oxygenator, or the dialyzer was brought into contact with the above mixed reaction solution, and allowed to react at room temperature for 1 to 48 hours.

B. The medical catheter, oxygenator, or dialyzer prepared by step A was washed and dried, thereby obtaining a medical catheter, an oxygenator, or a dialyzer coated with a nitric oxide-generating coating.

Example 52

A process for constructing a nitric oxide-generating adherent coating was as follows:

A. The nitric oxide-generating adherent coating could be applied to a medical catheter, an oxygenator, or a dialyzer by a simple dip coating method. EC, cystamine and copper sulfate were dissolved in the TRIS buffer of pH=5-12 to obtain a mixed solution in which each had a concentration of 1 mg/mL. Then, the medical catheter, the oxygenator, or the dialyzer was brought into contact with the above mixed reaction solution, and allowed to react at room temperature for 1 to 48 hours.

B. The medical catheter, oxygenator, or dialyzer prepared by step A was washed and dried, thereby obtaining a medical catheter, an oxygenator, or a dialyzer coated with a nitric oxide-generating coating.

Example 53

A process for constructing a nitric oxide-generating adherent coating was as follows:

A. The nitric oxide-generating adherent coating could be applied to a medical catheter, an oxygenator, or a dialyzer by a simple dip coating method. ECG, cystamine and copper sulfate were dissolved in a TRIS buffer of pH=5-12 to obtain a mixed solution in which each had a concentration of 1 mg/mL. Then, the medical catheter, the oxygenator, or the dialyzer was brought into contact with the above mixed reaction solution, and allowed to react at room temperature for 1 to 48 hours.

B. The medical catheter, oxygenator, or dialyzer prepared by step A was washed and dried, thereby obtaining a medical catheter, an oxygenator, or a dialyzer coated with a nitric oxide-generating coating.

Example 54

A process for constructing a nitric oxide-generating adherent coating was as follows:

A. The nitric oxide-generating adherent coating could be applied to a medical catheter, an oxygenator, or a dialyzer by a simple dip coating method. EGC, cystamine and copper sulfate were dissolved in a TRIS buffer of pH=5-12 to obtain a mixed solution in which each had a concentration of 1 mg/mL. The medical catheter, the oxygenator, or the dialyzer was then brought into contact with the above mixed reaction solution and allowed to react at room temperature for 1 to 48 hours.

B. The medical catheter, oxygenator, or dialyzer prepared by step A was washed and dried, thereby obtaining a medical catheter, an oxygenator, or a dialyzer coated with a nitric oxide-generating coating.

Example 55

A process for constructing a nitric oxide-generating adherent coating was as follows:

A. The nitric oxide-generating adherent coating could be applied to a metallic, polymeric or ceramic porous scaffold bone replacement material or a dental implant material by simple dip coating. GA, cystamine and copper chloride were dissolved in a TRIS buffer of pH=5-12 to obtain a mixed solution in which each had a concentration of 0.1 mg/mL. The metallic, polymeric or ceramic porous scaffold bone implant or the dental implant was then immersed in the above mixed reaction solution and allowed to react at room temperature for 1 to 48 hours.

B. The metallic, polymeric or ceramic porous scaffold bone implant or the dental implant prepared by step A was washed and dried, thereby obtaining a metallic, polymeric or ceramic porous scaffold bone implant or a dental implant coated with a nitric oxide-generating coating.

Example 56

A process for constructing a nitric oxide-generating adherent coating was as follows:

A. The nitric oxide-generating adherent coating could be applied to a metallic, polymeric or ceramic porous scaffold bone implant or a dental implant by a simple dip coating method. Dopamine, cystamine and copper chloride were dissolved in a TRIS buffer of pH=5-12 to give a mixed solution in which each had a concentration of 0.1 mg/mL. The metallic, polymeric or ceramic porous scaffold bone implant or the dental implant was then immersed in the above mixed reaction solution and allowed to react at room temperature for 1 to 48 hours.

B. The metallic, polymeric or ceramic porous scaffold bone implant or the dental implant prepared by step A was washed and dried, thereby obtaining a metallic, polymeric or ceramic porous scaffold bone implant or a dental implant coated with a nitric oxide-generating coating.

Example 57

A process for constructing a nitric oxide-generating adherent coating was as follows:

A. The nitric oxide-generating adherent coating could be applied to a metallic, polymeric or ceramic porous scaffold bone implant or a dental implant by a simple dip coating method. Norepinephrine, cystamine and copper chloride were dissolved in a TRIS buffer of pH=5-12 to obtain a mixed solution in which each had a concentration of 0.1 mg/mL. The metallic, polymeric or ceramic porous scaffold bone implant or the dental implant was then immersed in the above mixed reaction solution and allowed to react at room temperature for 1 to 48 hours.

B. The metallic, polymeric or ceramic porous scaffold bone implant or the dental implant prepared by step A was washed and dried, thereby obtaining a metallic, polymeric or ceramic porous scaffold bone implant or a dental implant coated with a nitric oxide-generating coating.

Example 58

A process for constructing a nitric oxide-generating adherent coating was as follows:

A. The nitric oxide-generating adherent coating could be applied to a metallic, polymeric or ceramic porous scaffold bone implant or a dental implant by a simple dip coating method. EGCG, cystamine and copper chloride were dissolved in a TRIS buffer of pH=5-12 to obtain a mixed solution in which each had a concentration of 0.1 mg/mL. The metallic, polymeric or ceramic porous scaffold bone implant or the dental implant was then immersed in the above mixed reaction solution and allowed to react at room temperature for 1 to 48 hours.

B. The metallic, polymeric or ceramic porous scaffold bone implant or the dental implant prepared by step A was washed and dried, thereby obtaining a metallic, polymeric or ceramic porous scaffold bone implant or a dental implant coated with a nitric oxide-generating coating.

Example 59

A process for constructing a nitric oxide-generating adherent coating was as follows:

A. The nitric oxide-generating adherent coating could be applied to a metallic, polymeric or ceramic porous scaffold bone implant or a dental implant by a simple dip coating method. Dopa, cystamine and copper chloride were dissolved in a TRIS buffer of pH=5-12 to give a mixed solution in which each had a concentration of 0.1 mg/mL. The metallic, polymeric or ceramic porous scaffold bone implant or the dental implant was then immersed in the above mixed reaction solution and allowed to react at room temperature for 1 to 48 hours.

B. The metallic, polymeric or ceramic porous scaffold bone implant or the dental implant prepared by step A was washed and dried, thereby obtaining a metallic, polymeric or ceramic porous scaffold bone implant or a dental implant coated with a nitric oxide-generating coating.

Example 60

A process for constructing a nitric oxide-generating adherent coating was as follows:

A. The nitric oxide-generating adherent coating could be applied to a metallic, polymeric or ceramic porous scaffold bone implant or a dental implant by a simple dip coating method. Catechol, cystamine and copper chloride were dissolved in a TRIS buffer of pH=5-12 to give a mixed solution in which each had a concentration of 0.1 mg/mL. The metallic, polymeric or ceramic porous scaffold bone implant or the dental implant was then immersed in the above mixed reaction solution and allowed to react at room temperature for 1 to 48 hours.

B. The metallic, polymeric or ceramic porous scaffold bone implant or the dental implant prepared by step A was washed and dried, thereby obtaining a metallic, polymeric or ceramic porous scaffold bone implant or a dental implant coated with a nitric oxide-generating coating.

Example 61

A process for constructing a nitric oxide-generating adherent coating was as follows:

A. The nitric oxide-generating adherent coating could be applied to an intervention catheter or guidewire by simple dip coating. GA, SeCA and copper chloride were dissolved in a TRIS buffer of pH=5-12 to obtain a mixed solution in which each had a concentration of 0.1 mg/mL. The intervention catheter or guidewire was then immersed in the above mixed reaction solution and allowed to react at room temperature for 1 to 48 hours.

B. The intervention catheter or guidewire prepared by step A was washed and dried, thereby obtaining an intervention catheter or guidewire coated with a nitric oxide-generating coating.

Example 62

A process for constructing a nitric oxide-generating adherent coating was as follows:

A. The nitric oxide-generating adherent coating could be applied to an acellular porcine heart valve by simple dip coating. GA, SeCA and copper chloride were dissolved in a TRIS buffer of pH=5-12 to obtain a mixed solution in which each had a concentration of 0.1 mg/mL. The acellular porcine heart valve was then immersed in the above mixed reaction solution and allowed to react at room temperature for 1 to 48 hours.

B. The acellular porcine heart valve prepared by step A was washed and dried, thereby obtaining an acellular porcine heart valve coated with a nitric oxide-generating coating.

What is claimed is:

1. A method for preparing a coating having nitric oxide (NO) generating activity which comprises:
    (a) mixing the following compounds in a buffer having a pH of 2 to 14 to form a reaction mixture:
        (i) one or more of compounds having an ortho-phenol structure, flavones, flavonols or dihydroflavones at a concentration of 0.1 ng/mL to 100 mg/mL,
        (ii) one or more of compounds having a disulfide bond, a diselenide bond, a monosulfide bond or a monoselenide bond selected from ebselen, cystamine and its derivatives, selenocystamine and its derivatives, selenocystine, cystine, L-selenocystamino acetic acid, cysteine and its derivatives, selenocysteine, acetylcysteine, L-selenomethionine, selenomethionine, S-methyl cysteine, S-ethyl cysteine, S-allyl cysteine, S-allyl mercaptocysteine and γ-glutamine cysteamine at a concentration of 0.1 ng/mL to 100 mg/mL, and
        (iii) one or more of soluble copper salts at a concentration of less than 100 mg/mL,
    (b) immersing a sample to be modified in the reaction mixture and allowing the reaction mixture and the sample to react at 0-200° C. for 1 second to 10 days; and
    (c) washing and drying the sample obtained from step (b) successively to obtain a target modified material.

2. The method according to claim 1, wherein:
    the compounds having the ortho-phenol structure are catechol and its derivatives, pyrogallic acid (PG), epicatechin (EC), epicatechin gallate (ECG), epigallocatechin (EGC), epigallocatechin gallate (EGCG), dopamine, norepinephrine, levodopa, D-dopa, gallic acid (GA) and its derivatives, and tannic acid (TA);
    the flavones are chrysin, tectochrysin, acacetin, apigenin and pectolinarigenin;
    the flavonols are izalpinin, galangin, rhamnetin, isorhamnetin, rhamnocitrin, kaempferide, ermanin, quercetin and derivatives thereof;
    the dihydroflavones are pinocembrin, pinostrobin, sakuranetin, isosakuranetin and naringenin.

3. The method according to claim 1, wherein the soluble copper salts are copper chloride ($CuCl_2$), cuprous chloride (CuCl), copper bromide (CuBr), cuprous bromide ($CuBr_2$), copper iodide (CuI), cuprous iodide ($CuI_2$), copper sulfate ($CuSO_4$), cuprous sulfate ($Cu_2SO_4$), copper nitrate ($Cu(NO_3)_2$), copper carbonate ($CuCO_3$), copper citrate ($C_6H_6CuO_7$), copper tartrate ($C_4H_4CuO_6.3H_2O$), copper propionate ($Cu(CO_2CH_3CH_2)_2$) and copper acetate ($Cu(CO_2CH_3)_2$).

4. The method according to claim 1, wherein the coating can be used for surface modification of a matrix with any geometric shape and material;
    the matrix includes metallic materials selected from the group consisting of stainless steel, cobalt-based alloys, titanium and alloys thereof, nickel-titanium alloys, platinum and alloys thereof, magnesium and alloys thereof, iron and alloys thereof, and zinc and alloys thereof; inorganic materials selected from the group consisting of titanium oxide and its nanotubes, carbonaceous materials (C), silicon, silicon dioxide, hydroxyapatite, calcium phosphate, silicon nitride ($Si_3N_4$), silicon carbide (SiC), aluminosilicate ($Na_2O.Al_2O_3.SiO_2$), calcium aluminum system ($CaO.Al_2O_3$), biological glass ($SiO_2.CaO.Na_2O.P_2O_5$), hydroxyapatite, calcium phosphate, and titanium nitride; polymer materials selected from the group consisting of terylene (PET), polyethylene (PE), polyvinyl chloride (PVC), polytetrafluoroethylene (PTFE), polyurethane (PU), polystyrene (PS), polyvinyl alcohol (PVALC), polypropylene (PP), polyoxymethylene (POM), polycarbonate (PC), polyurethane (PU), carbon copolymer (PDC), polyglycolic acid (PGA), polymethylmethacrylate (PMMA), polyvinyl acetate (PVA), polylactic acid (PLA), poly(lactic-co-glycolic acid) (PLGA), polytrimethylene carbonate (PTMC), polycaprolactone (PCL), polyhydroxyalkanoate (PHA), polybutylene succinate (PBS), polyamide (PA), polydioxane (PDS), epoxy resin (Epoxy), silicone rubber, silicone gel, polyacrylic acid (PAA) and its derivatives, polyethylene glycol and its derivatives, and polyvinyl alcohol (PVA); biomedical micro/nano-particles selected from the group consisting of ferroferric oxide nanoparticles, (mesoporous) silica nanoparticles (quantum dots), titanium oxide nanoparticles (quantum dots), and zinc oxide nanoparticles (quantum dots); natural biological materials selected from the group consisting of plastic starch-based materials (PSM), gelatin, collagen, sodium hyaluronate, fibrous protein, sodium alginate, agarose, silk protein, keratin, cellulose, hemicellulose, lignin, chitin and derivatives thereof, and animal derived acellular tissues and organs (blood vessel, valve, heart, bone, lung, ligament, bladder, mucosa, and cornea); synthetic peptide hydrogel materials selected from the group consisting of poly-L-lysine and poly-L-glutamic acid; and composite materials thereof.

5. The method according to claim 1, wherein diselenide bonds, disulfide bonds, copper ions and phenolic hydroxyl groups contained in the coating have a free radical scavenging function;
   selenide bonds, sulfide bonds and chelated copper ions contained in the coating also have a response function to reduced glutathione (GSH);
   in addition, copper ions contained in the coating also possess antimicrobial function;
   the coating, in addition to being used to catalyze the release of NO, can be applied to all areas related to free radical removal and GSH response functions.

* * * * *

UNITED STATES PATENT AND TRADEMARK OFFICE
CERTIFICATE OF CORRECTION

PATENT NO. : 10,736,996 B2  
APPLICATION NO. : 15/503172  
DATED : August 11, 2020  
INVENTOR(S) : Zhilu Yang et al.

Page 1 of 1

It is certified that error appears in the above-identified patent and that said Letters Patent is hereby corrected as shown below:

On the Title Page

At item (73) Assignees:
Change "Chengdu Southwest Jiaotong University Science and, Sichuan (CN); Chengdu Jiaoda Medical Science And Technology Comp, Chengdu, Sichuan (CN)" to -- GUANGZHOU NANCHUANG EVEREST MEDICAL TECHNOLOGY CO., LTD. GUANGZHOU, GUANGDONG PROVINCE (CN) --.

Signed and Sealed this  
Eighteenth Day of May, 2021

Drew Hirshfeld  
*Performing the Functions and Duties of the*  
*Under Secretary of Commerce for Intellectual Property and*  
*Director of the United States Patent and Trademark Office*